US006592747B2

(12) United States Patent
Horkans et al.

(10) Patent No.: US 6,592,747 B2
(45) Date of Patent: Jul. 15, 2003

(54) METHOD OF CONTROLLING ADDITIVES IN COPPER PLATING BATHS

(75) Inventors: Wilma Jean Horkans, Ossining, NY (US); Keith T. Kwietniak, Highlandfalls, NY (US); Peter S. Locke, Hopewell Junction, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/881,817

(22) Filed: Jun. 18, 2001

(65) Prior Publication Data

US 2003/0000850 A1 Jan. 2, 2003

(51) Int. Cl.$^7$ .............................................. G01N 27/42
(52) U.S. Cl. ........................ 205/787; 205/775; 208/434
(58) Field of Search ................................ 204/402, 434; 205/787, 794.5, 775

(56) References Cited

U.S. PATENT DOCUMENTS

| 4,474,649 A | * | 10/1984 | Goffman et al. ............ 204/400 |
| 4,479,852 A | * | 10/1984 | Bindra et al. ................ 204/434 |
| 5,192,403 A | | 3/1993 | Chang et al. |
| 5,196,096 A | * | 3/1993 | Chang et al. ................ 204/405 |
| 6,280,602 B1 | * | 8/2001 | Robertson .................... 205/775 |
| 6,365,033 B1 | * | 4/2002 | Graham et al. ............. 204/412 |

OTHER PUBLICATIONS

Freitag, W.O. et al, Determination of the Individual Additive Components in Acid Copper Plating Baths, *Plating 70* (10), Oct. 1983, pp. 55–60.

\* cited by examiner

*Primary Examiner*—Nam Nguyen
*Assistant Examiner*—Kaj K. Olsen
(74) *Attorney, Agent, or Firm*—Connolly Bove Lodge & Hutz, LLP; Robert M. Trepp, Esq.

(57) ABSTRACT

Organic addition agents in copper plating baths are monitored by diluting a sample of the bath with sulfuric acid and hydrochloric acid and optionally a cupric salt. The diluting provides a bath having conventional concentrations of cupric ion, sulfuric acid and hydrochloric acid; and adjusted concentrations of the organic addition agents of 1/X of their original values in the sample; where X is the dilution factor. CVS techniques are used to determine concentrations of organic addition agents.

16 Claims, No Drawings

METHOD OF CONTROLLING ADDITIVES IN COPPER PLATING BATHS

FIELD OF THE INVENTION

The present invention relates to monitoring and ultimately controlling organic additives and particularly the accelerator and suppressor components of the additives in copper plating baths. The copper plating baths can be used to deposit copper interconnections for semiconductor chips.

The present invention is especially advantageous for monitoring copper plating baths that comprise relatively high cupric ion concentrations and/or relatively low sulfuric acid concentration.

BACKGROUND OF THE INVENTION

Performance of semiconductor circuits can be limited by RC contributions from the on-chip interconnection structure, which may consist of up to 9 or more levels of conductor circuitry built in an insulating material. The R (resistance) factor in RC can be minimized by minimizing the resistivity of the conductive metal (i.e. maximizing its conductivity). To this end, the semiconductor industry is in the process of migrating from the traditional aluminum conductor to the more highly conducting copper in many high-performance products. The method of choice for the deposition of the copper conductor is electroplating, which, when used in combination with chemical-mechanical polishing, has been very successful in producing metal levels with good metal fill of the line and via features of the on-chip interconnection.

With each generation of technology, the feature dimensions become smaller and more challenging to fill even with the versatile electroplating technology. In very small features with high aspect ratios such as greater than 3, the rate of copper plating at the bottom of the feature may be limited by the rate of diffusion of Cu(II) ions in the plating bath. This phenomenon can cause voids in the copper lines; the resulting structures will have poor reliability and low yields in electrical tests. The ability of plating baths to fill very small, high aspect ratio features can be extended by increasing the Cu(II) concentration in the plating bath as disclosed in U.S. patent application Ser. No. 09/684,786 filed Oct. 10, 2000 and entitled "Electroplated Copper Interconnection Structure, Process for Making an Electroplating Bath" disclosure of which is incorporated herein by reference.

When the cupric sulfate concentration in a plating bath is increased, the sulfuric acid concentration must be decreased in order to stay below the saturation limit of cupric sulfate. Another motivation for decreasing the sulfuric acid concentration, independent of the cupric sulfate concentration, is to reduce the conductivity of the plating solution. In semiconductor wafer plating, use of low-conductivity plating baths can improve the wafer-scale metal distribution. When 300 mm wafers move into production, it is believed that lower-acid copper plating baths will be introduced into production.

Because of the high value of a very-large-scale integrated circuit chip, the manufacturing processes used in its fabrication must be tightly controlled. For copper plating, one of the most challenging problems is the control of the organic addition agents in the plating bath. The addition agent is a mixture of complicated organic compounds present at low concentrations in the plating bath. There are no truly specific and quantitative methods for separation and analyses of these compounds that can be practically used to control a manufacturing line.

One common monitoring method for organic plating additives is called CVS (for cyclic voltammetry stripping, the electrochemical technique that indirectly determines the solution concentrations of additives through their effects on the kinetics of the electrochemical copper deposition process). The baths for plating of copper wafer circuitry evolved from baths used to plate printed circuit boards. Although plating bath suppliers employ different, proprietary organic additives to control the copper properties, there is not much difference between suppliers in the recommended concentrations of the inorganic components of the plating bath. Typically, the baths have cupric sulfate concentrations on the order of about 0.25M and sulfuric acid compositions on the order of about 2N. They also contain traces of chloride, in the range of 1 to 4 mM.

The high-Cu(II), low-acid plating baths for improved fill as disclosed in U.S. patent application Ser. No. 09/684,786, on the other hand, are very different from these traditional baths in the concentrations of cupric sulfate and sulfuric acid. The cupric sulfate concentration can exceed 1M and the sulfuric acid concentration can be less than 0.25N. Installed CVS methods do not work well in these concentration ranges. Furthermore, it is conceivable that a manufacturing facility would simultaneously operate two plating baths, a traditional copper bath and a high-Cu(II), low-acid bath. It is thus desirable to use similar and compatible analytical methods to control the two kinds of baths.

SUMMARY OF THE INVENTION

The present invention is concerned with a method for monitoring the concentrations of the suppressor and accelerator organic addition agents in high-Cu(II) or low-acid copper plating baths. The method of the present invention is compatible both with the available commercial instrumentation and with procedures used for more typical copper plating baths.

Although plating baths may contain 4 or more low-concentration organic components in the additive, a practical approach is to control the additive as if it had only two components. These are usually named according to their affect on the kinetics of the electrochemical copper-deposition reaction. The suppressor is the portion of the additive that slows copper deposition; other common names for the suppressor are polarizer or leveler. The accelerator is the portion of the additive that increases the rate of copper deposition; other common names for the accelerator are depolarizer or brightener.

The present invention is a modification of the CVS analytical procedures for additives in copper plating baths to achieve two purposes: the modified procedures are more accurate for analyses in plating baths with high Cu(II) and/or low acid concentrations, and the operating conditions are compatible with more conventional acid copper plating baths (thus allowing operating of both kinds of baths in one facility with fewer complications in monitoring and control).

The copper plating baths monitored according the present invention comprise organic addition agents, cupric salt, sulfuric acid and hydrochloric acid. The copper plating baths contain a relatively high cupric ion concentration and/or a relatively low sulfuric acid concentration. The organic addition agents include a suppressor component and an accelerator component.

The process of the present invention comprises:
a) obtaining a sample of said bath;
b) diluting said sample with sulfuric acid and hydrochloric acid and optionally with a cupric salt to provide a composition comprising conventional concentrations of cupric ion, sulfuric acid and hydrochloric acid and adjusted concentrations of said organic addition agents of 1/X of their original values in said sample, where X is the dilution factor;

c) obtaining a standard solution of the suppressor component of the organic addition agent having conventional concentrations of cupric ion, sulfuric acid and hydrochloric acid and having a known concentration of the suppressor of 1/X of its target value in the plating bath;

obtaining a first stock solution having the same cupric sulfate, sulfuric acid, and hydrochloric acid concentrations as the diluted sample and optionally also having the accelerator at a concentration of 1/X of its target value in the plating bath;

obtaining a second stock solution having the same cupric sulfate, sulfuric acid, and hydrochloric acid concentrations as the diluted sample and also having a known amount of an electrochemically suppressing chemical;

performing a dilution titration CVS technique for determining the concentration of said suppressor component of the additive in the plating bath using said first stock solution and standardizing the analysis with said standard solution of the suppressor;

performing a standard-addition CVS technique for determining the concentration of said accelerator component of the additive in the plating bath, using said second stock solution and standard additions of the accelerator.

BEST AND VARIOUS MODES FOR CARRYING OUT THE INVENTION

The present invention is particularly useful in the analysis of high-Cu(II) and/or low-acid copper plating baths. These baths may be employed to extend the ability of electroplating technology to fill very small features with high aspect ratio in the fabrication of on-chip interconnection structures. Specifically, the invention is a method of determining the concentrations of the organic additives in high-Cu(II) and/or low-acid copper plating baths compatible with the common methods used for copper plating baths with conventional concentrations of Cu(II) and acid and using common analytical equipment. The analytical method is cyclic voltammetry stripping, CVS. The technique for additives known as suppressors is a CVS dilution-titration method. The technique for additives known as accelerators is a CVS standard-addition technique.

Preferred copper electroplating baths monitored according to the present invention contain a dissolved cupric salt wherein the concentration of the cupric salt is at least about 0.4 molar and preferably at least about 0.8 molar. The maximum amount is up to the solubility limit of the salt. The preferred salt is $CuSO_4$. The concentration of the cupric salt is typically about two to four times higher than the concentrations normally used in prior art baths.

In addition, the electroplating bath of the present invention can include up to about 0.5 molar of an inorganic acid. The electroplating bath more typically contains an amount up to about 0.5 molar, and preferably about 0.1 to about 0.25 molar concentration of an inorganic acid. The preferred acid is $H_2SO_4$. Alternatively propane sulfonic acid, methane sulfonic acid, hydrochloric acid, fluoboric acid, or other acids with comparable bath function can be added. The concentration of the acid is typically at least about three to four times lower than the concentration normally used in prior art electroplating baths.

The electroplating bath typically has an acidic pH, more typically up to about 5 and preferably about 1.

The electroplating baths preferably are free of complexing agents that are sometimes used present in electroplating baths with low acid concentration.

In addition the plating baths of the present invention contain small amounts of organic additives used to achieve superfilling and to control such properties of the electroplated copper as grain structure, ductility and trace impurities. Typical additives and their relative amounts are disclosed in PCT/US96/19592, disclosure of which is incorporated herein by reference.

One suitable system of additives is marketed by Enthone-OMI, Inc. and is known as Sabre Copper. The composition includes two additives one referred to as Sabre B and the other Sabre L. Two other suitable systems of additives are marketed by ShipleyRonal, Inc. One of them is known as the Copper Gleam 2001 system. The additives are referred to by the manufacturer as Copper Gleam 2001 Leveller and Copper Gleam 2001 Carrier. The other system of additives also marketed by ShipleyRonal Inc. is known as Nanoplate 2001 system, which is a two-additive configuration. One of the additives is referred to as C-2001 Suppressor Solution and the other is referred to as B-2001 Additive Solution. Another suitable system of additives is marketed by Atotech USA, Inc. and is known as the Cupracid HS system. The additives in this system are referred to by the manufacturer as Cupracid Brightener and Cupracid HS Basic Leveller.

Examples of specific additives which may be present in the bath in the instant invention are described in several patents. U.S. Pat. No. 4,110,176 issued Aug. 29, 1978 to H-G Creutz, deceased, et al., entitled "Electrodeposition of Copper" describes the use of additives in a plating bath such as poly alkanol quaternary-ammonium salt to give bright, highly ductile, low stress and good leveling copper deposits from an aqueous acidic copper plating bath, which patent is incorporated herein by reference.

U.S. Pat. No. 4,376,685 issued Mar. 15, 1983 to A. Watson, entitled "Acid Copper Electroplating Baths Containing Brightening and Leveling Additives", describes additives to a plating bath such as alkylated polyalkyleneimine to provide bright and leveled copper electrodeposits from an aqueous acidic bath, which patent is incorporated herein by reference.

U.S. Pat. No. 4,975,159 issued Dec. 4, 1990 to W. Dahms, entitled "Aqueous Acidic Bath for Electrochemical Deposition of a Shiny and Tear-Free Copper Coating and Method of Using Same", describes adding to an aqueous acidic bath combinations of organic additives including at least one substituted alkoxylated lactam as an amide-group-containing compound in an amount to optimize the brightness and ductility of the deposited copper, which patent is incorporated herein by reference. In U.S. Pat. No. 4,975,159, Table I lists a number of alkoxylated lactams which may be added to a bath in the instant invention. Table II lists a number of sulfur-containing compounds with water-solubilizing groups such as 3-mercaptopropane-1-sulfonic acid, which may be added to a bath in the instant invention. Table III lists organic compounds such as polyethylene glycol which may be added to a bath as surfactants in the instant invention.

U.S. Pat. No. 3,770,598 issued Nov. 6, 1973 to H-G Creutz, entitled "Electrodeposition of Copper from Acid Baths", describes baths for obtaining ductile, lustrous copper containing therein dissolved a brightening amount of the reaction product of polyethylene imine and an alkylating agent to produce a quaternary nitrogen, organic sulfides carrying at least one sulfonic group, and a polyether compound such as polypropylene glycol, which patent is incorporated herein by reference. U.S. Pat. No. 3,328,273 issued Jun. 27, 1967 to H-G Creutz et al., entitled "Electrodeposition of Copper from Acidic Baths", describes copper sulfate and fluoborate baths for obtaining bright, low-stress deposits with good leveling properties that contain organic sulfide compounds of the formula $XR_1$—(Sn)—$R_2$—$SO_3H$, where $R_1$ and $R_2$ are the same or different and are polymethylene groups or alkyne groups containing 1–6 carbon atoms, X is hydrogen or a sulfonic group, and n is an integer of 2–5 inclusive, which patent is incorporated herein by reference. Additionally, these baths may contain polyether compounds, organic sulfides with vicinal sulphur atoms, and phenazine dyes. In U.S. Pat. No. 3,328,273, Table I lists a number of polysulfide compounds which may be added to a bath in the instant invention. Table II lists a number of polyethers which may be added to a bath in the instant invention.

Additives may be added to the bath for accomplishing various objectives. For the application of on-chip interconnections, the additives may be included for inducing in the copper conductor specific film microstructures including large grain size relative to film thickness or randomly oriented grains.

The present invention relates to a modification of CVS analytical procedures for additives in copper plating baths.

The common CVS methods are dilution-titration for the suppressor and standard addition for the accelerator, or variations on these techniques. In essence, these are modifications of the known analytical methods of titration or standard addition, but employing a sensor that is sensitive to the copper deposition kinetics. This sensor is typically a platinum rotating disk electrode in an acid cupric sulfate solution; the platinum electrode undergoes cycling through a potential range that causes repeated plating of copper on the platinum disk and stripping (dissolution) of the plated copper. The stripping charge measures the amount of copper plated on the Pt, which, under constant cycling conditions, is a measure of the kinetics of copper deposition. Changes in the stripping charge during the analytical procedure indirectly measure the addition agents through their influence on the copper deposition rate. The dilution-titration and standard-addition methods and various comparable methods are available in the software of commercial instrumentation for CVS analysis of plating baths.

The dilution titration technique is described by Freitag et al., Plating 70(10), 55(1983), "Determination of the Individual Additive Components in Acid Copper Plating Baths." The suppressor analysis is based on the observation that an increase in suppressor concentration decreases the measured copper charge in CVS. For this technique, the copper stripping charge in cyclic voltammetry is measured first in a known volume of plating bath make-up (i.e. the inorganic components) without additive. This additive-free bath is then titrated with small aliquots of the working plating bath, and the decrease in copper stripping charge is measured as a function of the added bath volume. The procedure is calibrated by performing the same titration with a standard solution of make-up containing a known concentration of the additive. The normalized copper stripping charge is plotted against added volume for both the working bath and the standard. From these plots can be found the added volume required to reach a predetermined endpoint. The concentrations of the titrating solutions (the working bath and the standard bath) are inversely proportional to the volumes needed to reach this endpoint. Since the concentration of the standard is known, the concentration of the working bath can be calculated.

In some manufacturers' systems of plating additives, there can be interferences between the additive components in the analysis as taught by Freitag et al. An example is the Sabre plating chemistry manufactured by Enthone-OMI, a formulation commonly used in the Novellus Sabre plating tool. The two additive components of the Sabre chemistry are Sabre B, which has primarily an accelerating function, and Sabre L, which has primarily a suppressing function. The method of Freitag, et al. works poorly with Sabre L, however, because there is a subcomponent of Sabre B that interferes with the suppressor analysis in their embodiment. They implicitly recognize this fact and describe the result of their analysis as an effective concentration.

A more quantitative dilution-titration analysis of the suppressor additive is described by I-C. Chang and W. J. Horkans, U.S. Pat. No. 5,192,403, "Cyclic Voltammetric Method for the Measurement of Concentrations of Subcomponents of Plating Solution Additive Mixtures." The principle of this technique is that the solution into which the titration is done should contain all of the components of the plating solution except the component which is being determined. Thus, in the Sabre example above, the initial solution for the Sabre L analysis contains all of the inorganic components of the plating bath as well as the Sabre B additive at its target concentration in the plating bath.

As taught in U.S. Pat. No. 5,192,403, the dilution-titration uses the plating charge rather than the stripping charge. For copper plating baths, the plating charge is a more accurate measurement of the amount of copper plated, since the plating efficiency is essentially 100% but the stripping efficiency is measurably less than 100% in the presence of chloride ion, even in the presence of the low levels of chloride typical of commercial acid copper plating baths. The analytical error introduced by use of the stripping charge is negligible, however, and the technique can be practiced equally well measuring either the plating charge or the stripping charge in cyclic voltammetry.

Furthermore, U.S. Pat. No. 5,192,403 teaches the measurement of the very early part of the titration curve, which can be linearized. The invention of that patent, namely performing the titration in a stock solution containing all chemicals except the additive of interest, works equally well if the titration is performed over a much wider range of additive volume. In the nonlinear range, the dependence of CVS charge on titrant addition volume can be fit to a quadratic curve. The titrant volume required to reach a predetermined endpoint is inversely proportional to the concentration of the suppressor in the titrant solution. Since the concentration of suppressor in the standard is known, the concentration in the unknown plating bath can be determined from the ratio of titrant volumes at endpoint for the unknown and for the standard.

The standard addition technique for accelerator analysis is also based on the publication of Freitag, et al., Plating 70(10), 55(1983). They show that once a saturation concentration of the suppressor component is reached, addition of further accelerator component causes an increase in the copper stripping charge in CVS. An initial CVS measurement is made in a stock containing the inorganic components of the plating bath at their target values and a sufficient concentration of a suppressing species to reach saturation. A known volume of the unknown plating bath is added to this stock, and the CVS is measured again; the copper charge in CVS will have increased because of the introduction of the accelerating additive from the unknown plating bath. From further additions of the pure accelerating additive to determine the slope of the charge-concentration dependence, the concentration in the unknown plating bath can be calculated.

As described above, the dilution-titration and standard-addition methods of CVS are widely employed in the monitoring and control of the suppressor and accelerator components, respectively, of copper plating baths. They work adequately in conventional plating bath, but they have been unreliable in plating baths with higher Cu(II) concentration.

In the present embodiment of the dilution-titration analysis for the suppressor (preferably the method of U.S. Pat. No. 5,192,403 disclosure of which being incorporated herein by reference), the high-Cu(II), low-acid unknown plating bath is mixed with sulfuric acid and hydrochloric acid to achieve the typical concentrations of the inorganic species cupric sulfate, sulfuric acid, and hydrochloric acid. This mixing dilutes the additives by a known factor. The stock solution contains the typical concentrations of the inorganic species cupric sulfate, sulfuric acid, and hydrochloric acid, and the accelerator at a concentration of 1/X times its target value in the plating baths, where X is the dilution factor that was used for the unknown plating bath. The standard solution contains the typical concentrations of the inorganic species cupric sulfate, sulfuric acid, and hydrochloric acid, and the accelerator and suppressor both at 1/X times their target values in the plating baths, where X is the dilution factor that was used for the unknown plating bath.

The dilution factor X is typically at least about 1.5, more typically at least about 2 to about 5 and preferably about 4.

After this dilution and proper adjustment of the addition volumes of the titration, the usual dilution-titration CVS analysis (preferably the method of U.S. Pat. No. 5,192,403) can be performed.

In the standard-addition analysis for the accelerator according to the present invention, the high-Cu(II), low-acid bath is mixed with sulfuric acid solution to achieve the typical concentrations of the inorganic species cupric sulfate, sulfuric acid, and hydrochloric acid. This mixing dilutes the additives by a known factor X. The usual standard-addition CVS accelerator analysis can be used with the same suppressor stock that is used for typical copper plating baths. The analytical result is multiplied by the dilution factor X to obtain the accelerator concentration in the undiluted unknown copper plating bath.

The procedure below describes the embodiment of these techniques for one high-Cu(II), low-acid copper plating bath as described in U.S. patent application Ser. No. 09/684,786. The example is given for the commercially-available Sabre copper plating bath manufactured by Enthone-OMI. The suppressor additive in the Sabre plating bath is called Sabre L; the accelerator additive is called Sabre B.

The composition of a bath as described in U.S. patent application Ser. No. 09/684,786 is given in the table below.

| High-Cu(II) Bath Concentrations | |
|---|---|
| Component | Concentration |
| $CuSO_4 \cdot 5H_2O$ | 248 g/l |
| $H_2SO_4$ | 24 g/l |
| HCl | 70 mg/l |

-continued

| High-Cu(II) Bath Concentrations | |
|---|---|
| Component | Concentration |
| Sabre B | 0.1–20 ml/l |
| Sabre L | 0.1–5 ml/l |

For comparison, the composition of a more conventional copper plating bath employing the same additives is given in the table below.

| Conventional Bath Concentrations | |
|---|---|
| Component | Concentration |
| $CuSO_4 \cdot 5H_2O$ | 62 g/l |
| $H_2SO_4$ | 160 g/l |
| HCl | 70 mg/l |
| Sabre B | 0.1–20 ml/l |
| Sabre L | 0.1–5 ml/l |

The goal is to adjust the concentrations of the high-Cu(II) solution's inorganic components to the same values as those in the conventional plating bath to achieve commonality of the analytical techniques. In the example shown the high-Cu(II) requires a 4:1 dilution to match the cupric sulfate concentration of the conventional plating bath; the high-Cu(II) bath also requires an increase in sulfuric acid in order to match the sulfuric acid concentration of the conventional plating bath. This adjustment of the high-Cu(II) plating bath to the concentration of the conventional bath is achieved by using a 4:1 dilution with the following solution.

| Diluting Solution (for 1:4 dilution) | |
|---|---|
| Component | Concentration |
| $H_2SO_4$ | 205 g/l |
| HCl | 70 mg/l |

The suppressor analysis for the high-Cu(II) bath requires the preparation of three solutions: 1) a diluted bath sample; 2) a standard, either prepared full-strength and diluted according to the same procedure as the bath sample or prepared to the post-dilution concentrations; and 3) a stock solution in which the titration is to be performed. The preparation of the three solutions for the suppressor analysis is described below.

1) The diluted unknown bath sample is prepared by pipetting 25 ml of the high-Cu(II) plating bath into a 100 ml volumetric flask and diluting to volume with the dilution solution above. This process will have changed the concentration of the suppressor Sabre L to ¼ of its original value.

2) The diluted standard can either be prepared from a high-Cu(II), low-acid standard, or it can be prepared directly at the post-dilution concentrations. If the target concentrations of the Sabre L is 2 ml/l, the diluted standard should have the following concentrations.

| Sabre L Standard Equivalent to Diluted 2 ml/l Solution | |
|---|---|
| Component | Concentration |
| $CuSO_4.5H_2O$ | 62 g/l |
| $H_2SO_4$ | 160 g/l |
| HCl | 70 mg/l |
| Sabre B | 2.5 ml/l |
| Sabre L | 0.5 ml/l |

3) In the preferred analytical technique for suppressor determination, U.S. Pat. No. 5,192,403, the stock which is titrated contains all components other than the suppressor at their target concentrations in the plating bath, in this case at their concentrations after dilution. If the target concentration of Sabre B is 10 ml/1 in the undiluted bath, then the stock will have the following composition.

| Stock for Sabre L Analysis | |
|---|---|
| Component | Concentration |
| $CuSO_4.5H_2O$ | 62 g/l |
| $H_2SO_4$ | 160 g/l |
| HCl | 70 mg/l |
| Sabre B | 2.5 ml/l |

An example analysis was performed on a QP4000 CVS analyzer manufactured by ECI Technology. The routines described are those installed in the software of the QP4000. The DT3 dilution-titration method was selected, with a 50 ml sample volume and 3.5 ml addition volume. The standard concentration was entered as 2.0 ml/1 (although it was actually 0.5 ml/1), and no dilution factor was entered for the unknown solution. An endpoint of 0.6 and a stop point of 0.5 were used. The addition volume was adjusted depending on the concentration of the unknown sample.

The table below shows the analytical results for 5 test solutions. The largest error was 10%. In general, the results are within the expected accuracy.

| Sabre L Conc. (ml/l) | Addition Volume (ml) | CVS Result (ml/l) |
|---|---|---|
| 1.40 | 4.00 | 1.54 |
| 1.60 | 3.75 | 1.66 |
| 1.80 | 3.50 | 1.87 |
| 2.00 | 3.00 | 2.10 |
| 2.20 | 2.75 | 2.21 |

The accelerator analysis for the high-Cu(II) bath requires the preparation of two solutions: 1) a diluted bath sample; and 2) a suppressed stock solution with the same target concentrations of inorganic species as the diluted unknown. The preparation of the two solutions for the accelerator analysis is described below.

1) The diluted unknown bath sample is the same solution used in the suppressor analysis.

2) The stock can be suppressed with any of a variety of chemicals; it is typical to use polyethylene glycol, PEG, or a species with similar chemical functionality. The suppressed stock solution has the following post-dilution concentrations.

| Suppressed Stock for Sabre B Analysis | |
|---|---|
| Component | Concentration |
| $CuSO_4.5H_2O$ | 62 g/l |
| $H_2SO_4$ | 160 g/l |
| HCl | 70 mg/l |
| PEG | 2.0 g/l |

An example analysis was performed on a QP4000 CVS analyzer. The MLAT standard-addition method was selected. The conditions entered in the MLAT protocol were a 1.4 dilution and a solution volume used was 100 ml. Thus, 75 ml of the suppressed stock was added for the A0 measurement, and 25 ml of unknown solution was added for measurement of the intercept. The accelerator concentration for the standard addition was 1000 ml/1 (pure Sabre B). The addition concentration was 0.30 ml/1. The software has no provision for unknown dilutions, and so the result of the analysis must be multiplied by 4 to obtain the Sabre B concentration in the plating solution.

The analytical results for Sabre B are given below for five test solutions.

| Sabre B (ml/l) | Sabre L (ml/l) | Sabre B CVS Result (ml/l) |
|---|---|---|
| 5.0 | 1.8 | 5.2 |
| 7.0 | 1.8 | 7.2 |
| 10.0 | 1.8 | 10.8 |
| 12.0 | 1.8 | 13.6 |
| 10.0 | 2.2 | 10.8 |

These same solutions were analyzed by HPLC. (In these solutions, there was only a single peak detected in HPLC.) The accuracy of the technique is within the expected range for CVS determination of an accelerator.

| Sabre B (ml/l) | Sabre L (ml/l) | Sabre B HPLC Result (ml/l) |
|---|---|---|
| 5.0 | 1.8 | 4.1 |
| 7.0 | 1.8 | 6.85 |
| 10.0 | 1.8 | 10.7 |
| 12.0 | 1.8 | 11.3 |
| 10.0 | 2.2 | 9.2 |

It will be apparent to those skilled in the art that comparable protocols could be applied to copper plating baths of other compositions that lie outside of the common practice. For one example, a bath having a low acid concentration but conventional cupric sulfate concentration would be diluted with a second solution having a higher sulfuric acid concentration and the same concentrations of cupric sulfate and hydrochloric acid.

It will also be apparent to those skilled in the art that the dilution protocols of this invention can also be adapted to other standard CVS plating bath analyses. For instance, there are appearing new commercial three-additive plating baths that are said to be fully analyzable by CVS. In such baths, there are separate CVS analyses for the accelerator, suppressor, and leveler components of the system of organic additives. All solutions in each analysis can be diluted into the range of conventional concentrations for the inorganic components according to the teachings of the present invention.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A method of monitoring organic addition agents comprising a suppressor component and an accelerator component in a copper plating bath which comprises cupric salt, sulfuric acid and hydrochloric acid;

wherein the cupric salt concentration is at least about 0.4 molar or the sulfuric acid concentration is about 0.5 molar or less, or both;

which process comprises a) obtaining a sample of said copper plating bath;
b) diluting said sample with sulfuric acid and hydrochloric acid and with a cupric salt to provide a composition comprising conventional concentrations of cupric ion, sulfuric acid and hydrochloric acid, wherein said conventional concentration means about 62 g/l CuSO4.5H2O, about 160 g/l H2SO4, and about 70 mg/l HCl and adjusted concentrations of said organic addition agents wherein adjusted concentrations means of 1/X of their original values in said sample, where X is the dilution factor meaning the ratio of the volume after dilution to the volume before dilution;
c) obtaining a standard solution of the suppressor component of the organic addition agents having conventional concentrations of cupric ion, sulfuric acid and hydrochloric acid and having a known concentration of the suppressor at 1/X of its target value in the plating bath;

obtaining a first stock solution having the same cupric sulfate, sulfuric acid, and hydrochloric acid concentrations as the diluted sample;

obtaining a second stock solution having the same cupric sulfate, sulfuric acid, and hydrochloric acid concentrations as the diluted sample and also having a known amount of an electrochemically suppressing chemical;

performing a dilution titration cyclic voltammetry stripping (CVS) technique for determining the concentration of said suppressor component of the additive in the plating bath using said first stock solution and standardizing the analysis with said standard solution of the suppressor;

performing a standard-addition CVS technique for determining the concentration of said accelerator component of the additive in the plating bath, using said second stock solution and standard additions of the accelerator.

2. The method of claim 1 wherein said copper plating bath comprises at least about 0.4 molar concentration of said cupric salt; and said diluting reduces the cupric ion concentration to its conventional range.

3. The method of claim 2 wherein the concentration of the cupric salt is at least about 0.8 molar.

4. The method of claim 2 wherein the concentration of sulfuric acid is an amount up to about 0.5 molar; and said diluting increases said sulfuric acid to its conventional range.

5. The method of claim 2 wherein the concentration of the sulfuric acid is about 0.1 to about 0.25 molar.

6. The method of claim 1 wherein the cupric salt comprises $CuSO_4$.

7. The method of claim 1 wherein the concentration of sulfuric acid is an amount up to about 0.5 molar; and said diluting increases said sulfuric acid to its conventional range.

8. The method of claim 7 wherein the concentration of the sulfuric acid is about 0.1 to about 0.25 molar.

9. The method of claim 1 wherein said bath has an acidic pH.

10. The method of claim 1 wherein the bath has a pH of about 5 or lower.

11. The method of claim 1 wherein X is at least about 1.5.

12. The method of claim 1 wherein X is about 1.5 to about 5.

13. The method of claim 1 wherein X is about 4.

14. The method of claim 1 wherein said first stock solution further comprises the accelerator component of the additive at 1/X its target concentration value, where X is the dilution factor.

15. The method of claim 1 which further comprises adjusting concentrations of said organic addition agents to desired concentrations based upon the concentrations determined by said addition CVS techniques and said dilution-titration CVS technique.

16. A method of monitoring organic addition agents according to claim 1 wherein said first stock solution also contains the accelerator at a concentration of 1/X of its target value in the plating bath.

* * * * *